US012612601B2

(12) United States Patent
Cho et al.

(10) Patent No.: US 12,612,601 B2
(45) Date of Patent: Apr. 28, 2026

(54) USE OF CROSS-FLOW FILTRATION DEVICE FOR PREPARING FUNCTIONAL EXOSOME

(71) Applicants: EXOSTEMTECH CO., LTD., Ansan-si (KR); INDUSTRY-UNIVERSITY COOPERATION FOUNDATION HANYANG UNIVERSITY ERICA CAMPUS, Ansan-si (KR)

(72) Inventors: Yong Woo Cho, Seongnam-si (KR); Ji Suk Choi, Siheung-si (KR); Young Chan Choi, Chuncheon-si (KR); Seung Hee Cho, Ansan-si (KR); Binna Son, Cheonan-si (KR)

(73) Assignees: EXOSTEMTECH CO., LTD., Ansan-si (KR); INDUSTRY-UNIVERSITY COOPERATION FOUNDATION HANYANG UNIVERSITY ERICA CAMPUS, Asan-si (KR)

( * ) Notice: Subject to any disclaimer, the term of this patent is extended or adjusted under 35 U.S.C. 154(b) by 796 days.

(21) Appl. No.: 17/909,939

(22) PCT Filed: Mar. 16, 2021

(86) PCT No.: PCT/KR2021/003265
§ 371 (c)(1),
(2) Date: Sep. 7, 2022

(87) PCT Pub. No.: WO2021/187880
PCT Pub. Date: Sep. 23, 2021

(65) Prior Publication Data
US 2023/0106258 A1 Apr. 6, 2023

(30) Foreign Application Priority Data

Mar. 16, 2020 (KR) ........................ 10-2020-0032225

(51) Int. Cl.
*C12M 1/00* (2006.01)
*B01D 63/02* (2006.01)
*C12N 5/0775* (2010.01)

(52) U.S. Cl.
CPC ........... *C12N 5/0667* (2013.01); *B01D 63/02* (2013.01); *C12M 29/04* (2013.01); *C12M 47/10* (2013.01)

(58) Field of Classification Search
None
See application file for complete search history.

(56) References Cited

U.S. PATENT DOCUMENTS

| | | | |
|---|---|---|---|
| 2002/0197210 A1 | 12/2002 | Bednarski et al. | |
| 2013/0059782 A1 | 3/2013 | Murat Moreno et al. | |
| 2019/0391136 A1 | 12/2019 | Riazifar | |
| 2021/0238248 A1 | 8/2021 | Llorente et al. | |

FOREIGN PATENT DOCUMENTS

| | | | | |
|---|---|---|---|---|
| CA | 3 073 162 A1 | 2/2019 | | |
| EP | 1 997 545 A2 | 12/2008 | | |
| JP | 2004-525916 A | 8/2004 | | |
| JP | 2008-290044 A1 | 12/2008 | | |
| JP | 2013-525326 A | 6/2013 | | |
| KR | 10-1895916 B1 | 9/2018 | | |
| KR | 10-2018-0135411 A | 12/2018 | | |
| WO | WO-2017160739 A1 * | 9/2017 | ............ | B01D 61/20 |
| WO | 2019/238626 A1 | 12/2019 | | |
| WO | 2020/030817 A1 | 2/2020 | | |

OTHER PUBLICATIONS

Haraszti et al. Exosomes Produced from 3D Cultures of MSCs by Tangential Flow Filtration Show Higher Yield and Improved Activity. Mol Ther. Dec. 5, 2018;26(12):2838-2847. Epub Sep. 22, 2018. (Year: 2018).*
Worsham et al. Potential of Continuous Manufacturing for Liposomal Drug Products. Biotechnol J. Feb. 2019;14(2):e1700740. Epub Jun. 11, 2018. (Year: 2018).*
Masri et al. Challenges and advances in scale-up of label-free downstream processing for allogeneic cell therapies. Cell Gene Therapy Insights 2017; 3(6), 447-467. (Year: 2017).*
Jin Gao et al., "Generation, purification and engineering of extracellular vesicles and their biomedical applications", Methods, Nov. 30, 2019, vol. 177(2020), pp. 114-125.
Zhenjiang Zhang et al., "Engineering of Exosomes to Target Cancer Metastasis," Cellular and Molecular Bioengineering, Feb. 2020, vol. 13, No. 1.
Santiago Correa et al., "Highly Scalable, Closed-Loop Synthesis of Drug-Loaded, Layer-by-Layer Nanoparticles," Adv. Funct. Mater., 2016, pp. 991-1003, vol. 26.
Samuel E. Lohse et al., "A Simple Millifluidic Benchtop Reactor System for the High-Throughput Synthesis and Functionalization of Gold Nanoparticles with Different Sizes and Shapes," ACS Nano, May 1, 2013, pp. 4135-4150, vol. 7, Issue 5.
Jia Liu et al., "Functional extracellular vesicles engineered with lipid-grafted hyaluronic acid effectively reverse cancer drug resistance," Biomaterials, 2019, vol. 223, 119475.
Mitja L. Heinemann et al., "Bench top isolation and characterization of functional exosomes by sequential filtration," Journal of Chromatography A, 2014.

* cited by examiner

*Primary Examiner* — Valerie E Bertoglio
*Assistant Examiner* — Briana N Ebbinghaus

(57) ABSTRACT

The present disclosure relates to a new use of a tangential flow filtration device and a continuous concentration system for producing an ultra-high concentration medical exosome solution.

6 Claims, 13 Drawing Sheets

| | Tangential flow filtration | Ultrahigh speed centrifugation | Membrane filter filtration |
|---|---|---|---|
| Particle concentration(p/mL) | $3.08 \pm 0.44 \times 10^7$ | $5.07 \pm 0.88 \times 10^7$ | $8.23 \pm 0.15 \times 10^7$ |
| Total washing process time | < 10 min | 60 ~ 120 min | 30 ~ 60 min |
| Ratio of the number of particles with a size of 50-200 nm to the total number of particles(%) | $62.4 \pm 27.9$ | $52.9 \pm 18.9$ | $40.6 \pm 39.6$ |

| Example | Comparative example 1 | Comparative example 2 |
|---|---|---|
| Tangential flow filtration | Ultrahigh speed centrifugation | Membrane filter filtration |

Free-dye not removed

| Sample | Zeta potential (mV) |
|---|---|
| Intact exosome | -15.7 ± 6.19 |
| PEGylated exosome | -21.3 ± 8.42 |

| Sample | Peak 1 (size, nm) | Peak 2 (size, nm) | Peak 3 (size, nm) |
|---|---|---|---|
| Intact exosome | 168.3 nm (75.7%) | 28.91 nm (19.1%) | 8.155 nm (3.1%) |
| PEGylated exosome | 271.4 nm (79.1%) | 20.12 nm (13.8%) | 4200 nm (7.1%) |

| | Exosome #1 (5x10⁹ p/mL) | Exosome #2 (5x10⁹ p/mL) | Exosome #3 (5x10⁹ p/mL) | Average |
|---|---|---|---|---|
| Absorbance at 480 nm (a.u.) | 0.161 | 0.167 | 0.169 | 0.166 |
| Doxorubicin in Exosome (μg/particle) | 18.5 | 20.1 | 20.7 | 20.8±1.2 |

*Exosome production yield(particle/g) =
Number of exosome particles produced per conditioned media of 1g

| | Production yield | | |
| --- | --- | --- | --- |
| | Exosome (p/g) | Protein (μg/g) | Particle/Protein ratio (p/μg) |
| One time concentration (20-40 times concentration) | $3.1 \pm 0.3 \times 10^8$ | $10.47 \pm 3.14$ | $2.55 \pm 0.15 \times 10^7$ |
| Two times concentration (60-100 times concentration) | $2.9 \pm 0.6 \times 10^8$ | $5.82 \pm 0.88$ | $4.34 \pm 1.24 \times 10^7$ |

USE OF CROSS-FLOW FILTRATION DEVICE FOR PREPARING FUNCTIONAL EXOSOME

CROSS REFERENCE TO RELATED APPLICATIONS

The present application is a National Phase of International Application No. PCT/KR2021/003265 filed on Mar. 16, 2021, which claims the priority benefit of Korean Patent Application No. 10-2020-0032225, filed on Mar. 16, 2020, in the Korean Intellectual Property Office, the disclosures of which are incorporated herein by reference.

TECHNICAL FIELD

The present disclosure relates to a novel use of a tangential flow filtration device and a continuous concentration system for producing an ultra-high concentrated exosome solution for medical use.

BACKGROUND ART

It is known that various cells present in multicellular organisms including humans, secret nano-sized endoplasmic reticulum called 'exosomes' Exosomes are vesicles with the same membrane structure as a cell membrane, and are known to play a role in delivering membrane components, proteins, RNA, and the like to other cells and tissues. In particular, exosomes secreted from stem cells contain various growth factors and cytokines secreted by stem cells, and are known to control behaviors such as cell adhesion, growth, differentiation, and the like. In addition, exosomes can be safely used while having the same effect as that of a cell culture solution, as impurities such as cell wastes, antibiotics, serum and the like in the cell culture solution are removed, in the process of separating.

Exosomes have a size of approximately 100 nm and perform cell-to-cell signaling. In particular, when a role as a transport mediating means of exchange of proteins and genetic materials and the like between cells is revealed, studies for controlling behaviors of tissues including cells using exosomes are in the spotlight.

Exosomes are known as materials that maximize the ability to deliver proteins and genetic materials derived from parent cells to specific cells. These exosome therapeutics have therapeutic efficacy that exceeds "Cytokine effect" of conventional cell therapeutics in terms of the efficacy of delivering proteins and genetic materials with therapeutic efficacy to cells around lesion tissues to treat the tissues. For control or analysis of properties of exosomes, research to give functionality by reacting a specific substance to a double lipid membrane or inside of exosomes is being conducted.

Numerous documents are referenced throughout the present description and citations thereof are indicated. The disclosures of the cited documents are incorporated in the present description by reference in their entirety to more clearly describe the level of the art to which the present disclosure pertains and the content of the present disclosure.

DISCLOSURE

Technical Problem

An object of the present disclosure is to provide a novel use of a conventional tangential flow filtration device which has been limited to concentration, purification and buffer exchange methods, and is to provide a method for preparing functional exosomes using only the tangential flow filtration device.

In addition, an object of the present disclosure is to provide a multiple TFF continuous concentration device for ultra-high concentration of exosomes from a solution comprising exosomes (e.g., stem cell culture solution) and a method for producing an ultra-high concentrated exosome solution.

More specifically, an object of the present disclosure is to provide the following embodiments.

Embodiment 1. A method of preparing functional exosomes, comprising modifying exosomes with functional materials using a tangential flow filtration (TFF) device.

Embodiment 2. The method of according to Embodiment 1, wherein the functional materials are one or more selected from the group consisting of a biocompatible polymer, a protein drug, a chemical drug and a labeled molecule.

Embodiment 3. The method according to any one of the preceding embodiments, wherein the method comprises the following steps: a reaction step of modifying exosomes with functional materials by mixing exosomes and functional materials in a mixed solution; a filtration and concentration step of removing unreacted functional materials; and a washing step of substituting a solvent of the mixed solution, wherein the reaction step, the filtration and concentration step, and the washing step are performed using a tangential flow filtration device (a first TFF device).

Embodiment 4. The method according to any one of the preceding embodiments, wherein the reaction step is performed in a process of circulating the mixed solution of the exosomes and the functional materials by a pump of the TFF device.

Embodiment 5. The method according to any one of the preceding embodiments, wherein the method does not use a separate batch reactor for reacting the exosomes and the functional materials.

Embodiment 6. The method according to any one of the preceding embodiments, wherein the method does not use a separate stirring facility and a separate washing facility other than the TFF device.

Embodiment 7. The method according to any one of the preceding embodiments, wherein the method performs the reaction step, the filtration and concentration step and the washing step simultaneously using the TFF device.

Embodiment 8. The method according to any one of the preceding embodiments, wherein the method is for large-scale production of the functional exosomes.

Embodiment 9. The method according to any one of the preceding embodiments, wherein the method further comprises a step of injecting concentrated functional exosomes obtained from the first TFF device into a multiple TFF continuous concentration device to further concentrate the exosomes, wherein the multiple TFF continuous concentration device comprises n TFF devices, and the n TFF devices are connected to form an one closed system insulated from outside, and n concentration processes are continuously performed in the one closed system, and wherein the n is an integer of 1 to 10.

Embodiment 10. A method for preparing an ultra-high concentrated exosome solution comprising: injecting a raw material solution comprising exosomes into a multiple TFF continuous concentration device in which n TFF devices are connected to form an one closed system isolated from outside; and continuously performing n concentration processes in the one closed system using the multiple TFF continuous concentration device, wherein the n is an integer of 1 to 10.

Embodiment 11. The method according to any one of the preceding embodiments, wherein concentration of exosomes in the final ultra-high concentrated exosome solution obtained after the continuous n concentration processes is 25 to $50^n$ times more concentrated than concentration of exosomes in the raw material solution.

Embodiment 12. The method according to any one of the preceding embodiments, wherein the concentration of exosomes in the final ultra-high concentrated exosome solution after the continuous n concentration processes is $10^7$ to $10^{13}$ particle/mL.

Other objects and advantages of the present disclosure will become more apparent from the following detailed description of the invention, claims and drawings.

Technical Solution

Novel Use of Tangential Flow Filtration Device for Producing Functional Exosomes One aspect of the present disclosure is to provide a method for production of functional exosomes, characterized by modifying exosomes to functional materials using a tangential flow filtration (TFF) device.

"Functional exosomes" refers to exosomes to which a biochemical function is imparted by loading or crosslinking functional materials such as biochemical molecules within the exosomes or inside/outside double-lipid membrane of the exosomes, and depending on the types and functions of the functional materials, it can be selectively applied to one or more selected from exosome labeling technology, exosome drug loading technology, exosome treatment technology, and the like.

The conventional technologies of preparing functional exosomes are carried out through a step-by-step process comprising ① a reaction process of exosomes and functional materials, ② a separation and purification process of functional exosomes, and ③ a complete product production process through additional concentration or dilution.

In the reaction process, after loading the exosomes and functional materials in a reactor or container, the functional materials and exosomes are reacted under a stirring environment. Then, in a process of transferring, incorporation of a foreign substance may occur. In addition, in order to create the stirring environment, an additional device such as a magnetic stirrer or a propeller stirring system, or the like is required.

In the separation and purification process, using ultracentrifugation or dialysis, unreacted residues are removed. The ultracentrifugation refers to a method of obtaining pure property-modified exosomes by diluting a large amount of buffer in a reactant to remove unreacted substances and performing ultracentrifugation. Residual reactants cannot be completely removed in a single process, and residual reactants can be completely removed through repeated washing 3 times or more. By requiring repeated ultracentrifugation, the yield of exosomes may be very low. In addition, it requires a high rotation speed of 150,000×g or more and a processing time of 1 hour or more per cycle. The dialysis refers to a method of removing residual reactants by a dialysis membrane that is smaller than exosomes and has a greater filtration function than reactants. It is a method of immersing exosome reactants contained in a dialysis tube in a large amount of buffer solution to remove residual reactants outside the dialysis tube, and a long washing time is required to obtain pure exosomes.

As such, in the conventional exosome-modifying technologies, commonly, 1) the reaction process and separation and purification process, and washing process are not simultaneously conducted, and 2) a repetitive and time-consuming washing process is required to remove residual reactants.

In addition, the conventional technologies of producing functional exosomes are only suitable for modifying exosomes of less than 100 mL at a time, and if they are scaled up to a commercial level, the process time and cost are significantly increased as well as exosome loss may occur.

Under this circumstance, the present disclosure provides a method for producing scaled-up exosomes at a commercial level by not only performing a reaction process, a separation and purification process and a washing process of functional exosomes using a tangential flow filtration device at the same time, but also producing a large amount of functional exosomes in a short time.

In general, the tangential flow filtration device comprises 1) a process of circulating a biological solution, 2) a process of removing proteins and impurities with a smaller size than a filtration filter, and 3) a process of substituting a solvent of the solution.

According to one embodiment of the present disclosure, in the 1) process, while mixing and reacting exosomes and functional materials, exosome surface modification is performed. Then, the mixed solution of the exosomes and functional materials is circulated by a pump, so there is no need to add a separate stirring process.

In the 2) process, unreacted functional materials such as proteins, dyes, polymers, and the like not participating in the reaction are removed by filtration, and a solution comprising reacted exosomes can be obtained. It may comprise a process of recirculating the solution comprising reacted exosomes and concentrating to a desired concentration.

In the 3) process, to remove residual reaction impurities, solvent substitution with a buffer solution or injection water, and for example, the solvent may be one or more selected from Phosphate-buffered saline (PBS), tris-buffered saline (TBS), 4-(2-hydroxyethyl)-1-piperazineethanesulfonic acid (HEPES)-buffered saline (HBS) physiological saline solution, distilled water, culture media and injection water.

Therefore, the present disclosure provides a method of production of functional exosomes, characterized by comprising a reaction step which mixes exosomes and functional materials; a filtration and concentration step which removes unreacted functional materials; and a washing step which substitutes a solvent of an exosome solution, and performing the reaction step, filtration and concentration step and washing step using one tangential flow filtration device.

When producing the surface-modified exosomes through the above series of processes, a separate batch reactor, a stirring facility and a washing facility are unnecessary, and additional concentration and washing except for the reaction time may be performed in a short time.

As such, the present disclosure provides a new method for producing functional exosome using a tangential flow filtration method utilized for a limited use including conventional separation and filtration, concentration, and performs a reaction step (biochemical modification of exosomes), a filtration and concentration step, and a washing step at the same time without a separate washing and stirring process, and therefore, higher productivity and yield than the conventional technologies can be obtained.

The tangential flow filtration device used in one embodiment of the present disclosure is an ultrafiltration system, and as the result of performing the reaction step, filtration and concentration step and washing step using the TFF device, the exosome solution can be efficiently concentrated up to a volume of $\frac{1}{10}$ to $\frac{1}{100}$.

Ultrafiltration, which is located in the middle of microfiltration and reverse osmosis, is a method of separating specific substances by the size difference between membrane pores and solutes. The ultrafiltration membrane is a molecular weight cutoff (MWCO) defined as the minimum molecular weight of a solute that exhibits 90% or more exclusion by the membrane, and can exhibit its separation performance.

The tangential flow filtration used in the present disclosure may be one or more selected from the group consisting of a hollow fiber TFF and a membrane TFF capable of performing ultrafiltration, and preferably, it may use a TFF filter having a molecular weight cutoff (MWCO) of 100,000 Da to 500,000 Da.

In the present disclosure, the term "modification" means loading or crosslinking functional materials (e.g.: biochemical substances) on the surface of the double lipid membrane of exosomes or inside of exosomes.

In one embodiment, the functional material may be one or more selected from the group consisting of a biocompatible polymer, a protein drug, a chemical drug and a labeling molecule.

The biocompatible polymer may be one or more selected from the group consisting of hyaluronic acid (HA), gelatin, chitosan, collagen, alginic acid, pectin, carrageenan, chondroitin, chondroitin sulfate, dextran, dextran sulfate, polylysine, carboxymethyl chitin, fibrin, agarose, pullulan, cellulose, polyvinyl pyrrolidone (PVP), polyethylene glycol (PEG), polyvinyl alcohol (PVA), hydroxypropyl cellulose (HPC), hydroxyethyl cellulose (HEC), hydroxypropylmethyl cellulose (HPMC), sodium carboxymethyl cellulose, polyalcohol, gums, Arabic gum, alginate, cyclodextrin, dextrin, glucose, fructose, starch, trehalose, glucose, maltose, lactose, lactulose, fructose, turanose, melitose, melezitose, dextran, sorbitol, xylitol, palatinate, polylactic acid, polyglycolic acid, polyethyleneoxide, polyacrylic acid, polyacrylamide, polymethacrylic acid, and polymaleic acid.

The protein drug may be one or more selected from the group consisting of hormones, cytokine, enzyme, antibodies, growth factors, transcription regulating factors, blood factors, vaccines, structure proteins, ligand proteins and receptors, cell surface antigens, receptor antagonists and toxins.

The chemical drug may be one or more selected from the group consisting of alkylating agents, antimetabolites, anthracyclines, plant alkaloids, topoisomerase inhibitors and anticancer agents (cyclophosphamide, methotrexate, 5-fluorouracil, vinorelbine, doxorubicin, docetaxel, bleomycin, vinblastine, dacarbazine, mustang, vincristine, procarbazine, prednisolone, etoposide, epirubicin, etc.).

The labeling molecule may be one or more selected from the group consisting of fluorophores (fluorescein, phycoerythrin, rhodamine, lissamine, and Cy3 and Cy5 (Pharmacia), etc.), chromophores, chemical luminophores, magnetic particles, radioactive isotopes ($C^{14}$, $I^{25}$, $P^{32}$ and $S^{35}$, etc.), labels, electron concentrated particles, enzymes (alkaline phosphatase and horseradish peroxidase, etc.), cofactors, substrates for enzymes, heavy metals (for example, gold), and antibodies, streptavidin, biotin, digoxigenin, and heptane having a specific binding partner such as a chelating group.

In one embodiment of the present disclosure, exosomes modified by functional materials may be exosomes secreted when primary cells such as stem cells, cancer cells, tissue cells, and the like, and cell lines such as stem cell lines, cancer cell lines and the like are cultured.

The stem cell lines may be one or more selected from the group consisting of embryonic stem cell lines, adult stem cell lines and induced pluripotent stem cell (iPSC) lines, and the cancer cell lines may be one or more selected from the group consisting of bladder cancer cell lines, blood cancer (leukemia, myeloma) cell lines, bone cancer cell lines, brain cancer cell lines, breast cancer cell lines, cervical cancer cell lines, colorectal cancer cell lines, endometrial cancer cell lines, esophageal cancer cell lines, fibrosarcoma cell lines, kidney cancer cell lines, liver cancer cell lines, lung cancer cell lines, lymphoma cell lines, nerve cancer cell lines, oral cancer cell lines, ovarian cancer cell lines, pancreatic cell lines, prostate cancer cell lines, skin cancer cell lines, spleen cancer cell lines, stomach cancer cell lines, testicular cancer cell lines, thyroid cancer cell lines and uterine cancer cell lines.

Functional exosome modified by the method of production of the present disclosure as described above can be mass-produced, thereby being usefully used for a medical use or a cosmetic use.

Continuous Concentration System for Production of Ultra-High Concentration of Medical Exosome Solution Other aspect of the present disclosure is to provide a continuous concentration system for production of an ultrahigh concentration of a medical exosome solution.

The conventional technology to concentrate exosomes currently includes ultracentrifugation, ultrafiltration, chromatography, precipitation methods of exosomes secreted by cells from a culture solution obtained in a cell culture process.

However, the presently reported exosome production conventional technology can only achieve 25 to 100-fold concentration compared to the initial capacity, and it is possible to produce exosomes at a concentration of $2.0 \times 10^{10}$ particle/mL at maximum. It is suitable for application such as cosmetics that have effective efficacy even at a low concentration, but additional concentration procedures may be required for clinical application at a low concentration or low capacity (articular cavity local injection with a very small volume, etc.). For a specific example, when $1.0 \times 10^{12}$ exosomes are an effective dose for treatment, 50 mL will have to be administered to be effective at present, and a method capable of administering such a large volume is only possible by intravenous injection. In addition, a low concentration of exosome therapeutic agent has a very high possibility of deviated from an application site during local injection, which may show a disadvantage of lowering the exosome treatment efficacy.

Currently, in order to produce a high concentration of exosome solution, an additional concentration process is required, and thus the number of processes or process time becomes long. The number of processes or process time is a process factor that has an absolute influence on production manpower and production cost, and addition of a process causes a decrease in productivity. Furthermore, depending on movement of an intermediate product or external exposure according to addition of a process, a factor that reduces stability of a therapeutic agent such as sample contamination by external factors may occur.

The present disclosure provides a method for producing an ultra-high concentration of exosome solution as a continuous process, by injecting a solution comprising exosomes (e.g.: stem cell culture solution) into a continuous concentration system as a raw material substance, which solves such a conventional problem.

Specifically, the present disclosure provides a method for producing an ultra-high concentration of exosome solution comprising injecting a raw material solution comprising exosomes into a multiple TFF continuous concentration device in which n TFF devices are connected as one system isolated from the outside; and continuously performing n concentration processes using the multiple TFF continuous concentration device in one closed system (herein, the n is an integer of 1 to 10).

"Continuous concentration system" means continuously performing a number of concentration processes in one closed system, by omitting an intermediate product recovery and raw material injection process in 2 or multiple TFF concentration processes, as illustrated in FIG. 12 to FIG. 14.

Specifically, the double and multiple TFF continuous concentration system is constructed as one system isolated from the outside, and the initially injected raw material culture solution undergoes a secondary or multiple concentration process simultaneously without product recovery after the primary concentration to produce the final raw material.

The system minimizes contamination by external factors generated by movement of intermediate products, and the like, thereby exhibiting improvement of stability and quality of the exosome solution.

Even in the conventional exosome extraction technology, there is an example of adding secondary TFF concentration to extract a high concentration of exosomes, but in the present disclosure, double or multiple concentration processes are simultaneously performed, t hereby reducing the process time and also increasing the concentration of the final product by 25 times or more. Therefore, it can be said that it is different from simply adding the convention concentration process.

In addition, in the present disclosure, system scale-up is possible, and a culture solution is not exposed to the outside during the concentration process at all, and thus medical stability can be secured, so it is suitable for pharmaceutical GMP application. In particular, the present system does not need to force process operation in BSC when GMP is applied, which is a factor that lowers workability and working difficulty. However, in the present system, BSC outside working after obtaining APV certification is possible.

The present disclosure consists of 1 TFF filter and 1 or more raw material injection container, 1 recovery container and a manifold per 1 concentration part.

The present disclosure continuously progresses double or multiple concentration parts.

1) For the primary TFF filter part, the filter capacity is selected according to the scale.

2) The secondary TFF filter part has a scale of $\frac{1}{10}$ to $\frac{1}{50}$ times in the primary filter part, and the filter capacity is selected according to the scale.

3) The (n)th TFF filter part has a scale of $\frac{1}{10}$ to $\frac{1}{50}$ times in the (n−1)th filter part, and the filter capacity is selected according to the scale.

2 to 5 of the filter parts may be applicable, but preferably, 2 to 3 parts may be applied, depending on the use and scale. However, it is not limited thereto.

The single filter part conducts 5 to 50-fold concentration, but preferably, conducts 10 to 30-fold concentration, based on the initial weight. However, it is not limited thereto.

The TFF filter may be used in both a sheet type and a hollow fiber type, but preferably, 10 to 30-fold concentration is conducted. However, it is not limited thereto.

The TFF filter may be selectable according to the capacity, but a filter having a shear rate of 1000 to 6,000 s−1 during operation should be selected, and preferably, a filter having 3,000 to 5,000 s−1 should be selected.

In the present disclosure, the concentration of the exosomes finally obtained during the (n)th continuous concentration theoretically provides 25 to 50 n-fold concentration, or preferably, provides 25 to 2500-fold concentration, or more preferably, provides 50 to 100-fold concentration, based on the initial raw material weight.

Specifically, the final exosome product obtained in the present disclosure is produced at an exosome concentration of $10^7$ to $10^{13}$ particle/mL, preferably, an exosome concentration of $2.0 \times 10^{10}$ to $5.0 \times 10^{10}$ particle/mL. However, in the present disclosure, it is not limited thereto.

On the other hand, the protein concentration of the final exosome product obtained in the present disclosure may be 1 to 1000 m/mL, preferably, 100 to 500 µg/mL, more preferably, 300 to 400 µg/mL. However, in the present disclosure, it is not limited thereto.

As a specific example of the present disclosure, the system provides an injection formulation for local injection comprising a high concentration of stem cell exosomes.

The injection formulation may have an exosome concentration of $1.0 \times 10^7$ to $1.0 \times 10^{13}$ particle/mL, and have a capacity of 0.1 to 100 mL.

MODE FOR INVENTION

Hereinafter, the present disclosure will be described in more detail by the following examples. However, the following examples illustrates the content of the present disclosure only, but does not limit the scope of the present disclosure. That those skilled in the art to which the present disclosure pertains can easily infer from the detailed description and examples of the present disclosure is construed as belonging to the scope of the present disclosure.

EXAMPLE

1. Human Adipose Derived Stem Cell Culture

In order to extract exosomes from human adipose derived stem cells, human adipose derived stem cells subcultured by passages 3 to 7 were cultured for 6 hours to 3 days and a cell culture solution was recovered. In the recovered cell culture supernatant, cell debris and impurities were removed using a 0.2 μm filter.

2. Human Adipose Derived Stem Cell Exosome Extraction

From the human adipose derived stem cell culture solution obtained in the 1, exosomes were extracted and purified using a Tangential Flow Filtration System. As a filter of the tangential flow filtration system, a filter having a 100 or 500 kDa filtering ability was used, and the cell culture solution was concentrated by 10 times or 100 times to recover exosomes. In order to increase the purity of the exosomes, the recovered exosomes were diluted in DPBS in a volume of 10 times to 100 times, and they were concentrated using a filter having a 100 or 500 kDa filtering ability once again. The extraction process was illustrated in FIGS. 3, 4.

3. Human Adipose Derived Stem Cell Exosome Properties Analysis

The physical and biochemical properties of the exosomes extracted from the human adipose derived stem cells through the 2 were confirmed by protein quantification using nanoparticle tracking analysis (NTA) and Bicinchonic Acid (BCA) assay methods. The size of the exosome particles extracted in the 2 was confirmed as 50 to 200 nm.

4. Fluorescence Labeled Functional Exosome Production (1) Production of Fluorescence Labeled Functional Exosomes Using Tangential Flow Filtration Method (Example)

Figure 1:
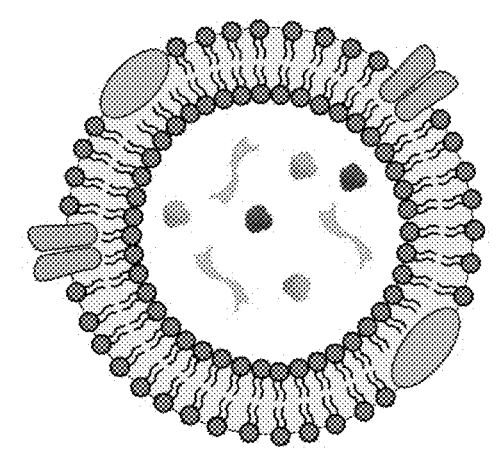
FIG. 1 is a schematic diagram of a stem cell exosome.
Figure 2:
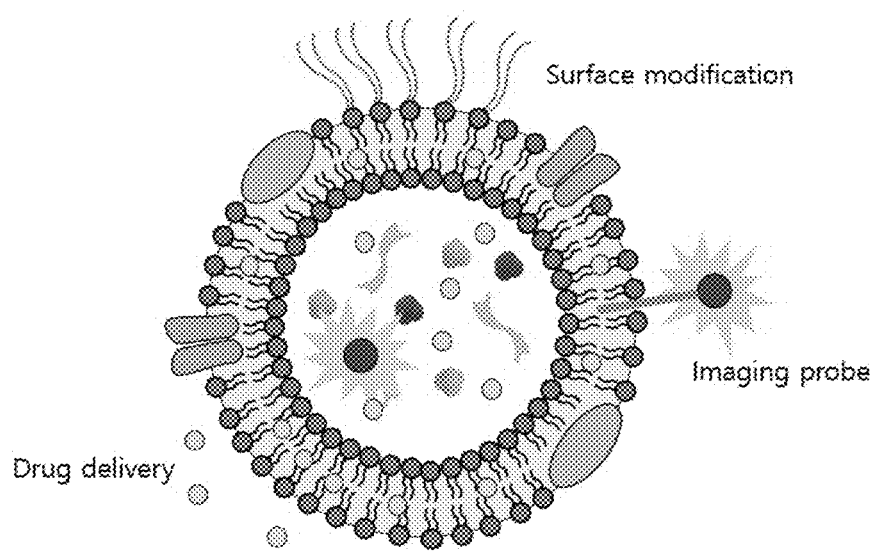
FIG. 2 is a schematic diagram of a functional exosome.
Figure 3:
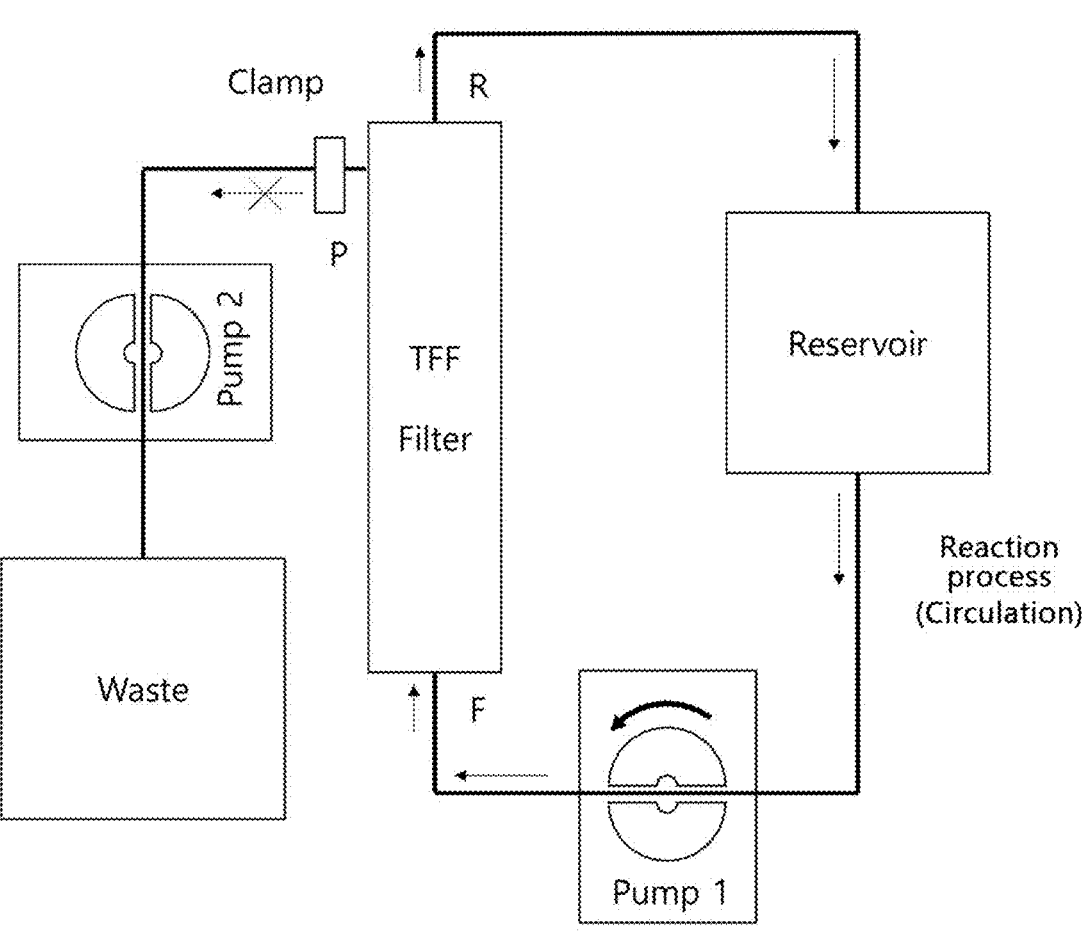
FIG. 3 is a schematic diagram of tangential flow filtration in the functional exosome reaction process.
Figure 4:
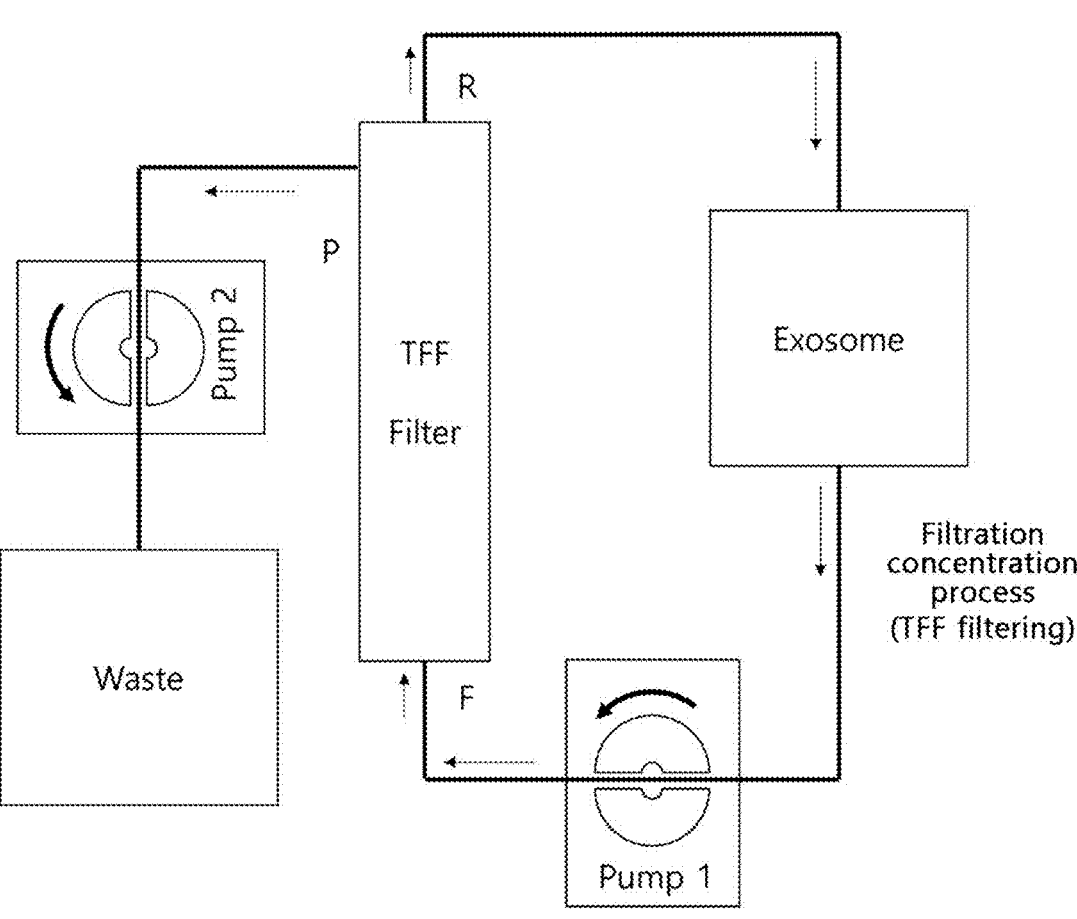
FIG. 4 is a schematic diagram of tangential flow filtration in the functional exosome filtration and concentration process and washing process.

The TFF device for producing fluorescence labeled functional exosomes was illustrated in FIG. 3 and FIG. 4. Exosomes 1 mL at a concentration of $5.0 \times 10^9$ particle/mL and fluorescence labeling materials of 100 uL (Vybrant™ DiD Cell-Labeling Solution, ThermoFisher Scientific, V22887) were transferred to a 1.5 mL tube. The mixture was diluted in DPBS in a volume of 10 times to 100 times, and was poured into a reservoir in the TFF device, respectively, and mixed.

Using the TFF device illustrated in FIG. 3, a process of circulating the exosomes and fluorescence labeled material and reacting them was conducted. The tube connected to the P (Permeate) direction of the TFF filter and PBS for washing blocked the tube connected to the reservoir with a clamp to prevent reactants from escaping to the outside or external buffer from being mixed. Pump 1 was operated at a speed of 10 to 100 cc/min for 10 seconds to 1 hour, so that the mixed solution of the exosomes and fluorescence labeling materials in the reservoir circulated inside the TFF filter. In the process, the fluorescence labeling materials were loaded on the exosome membrane, and the exosome surface was fluorescently labeled.

Figure 5:
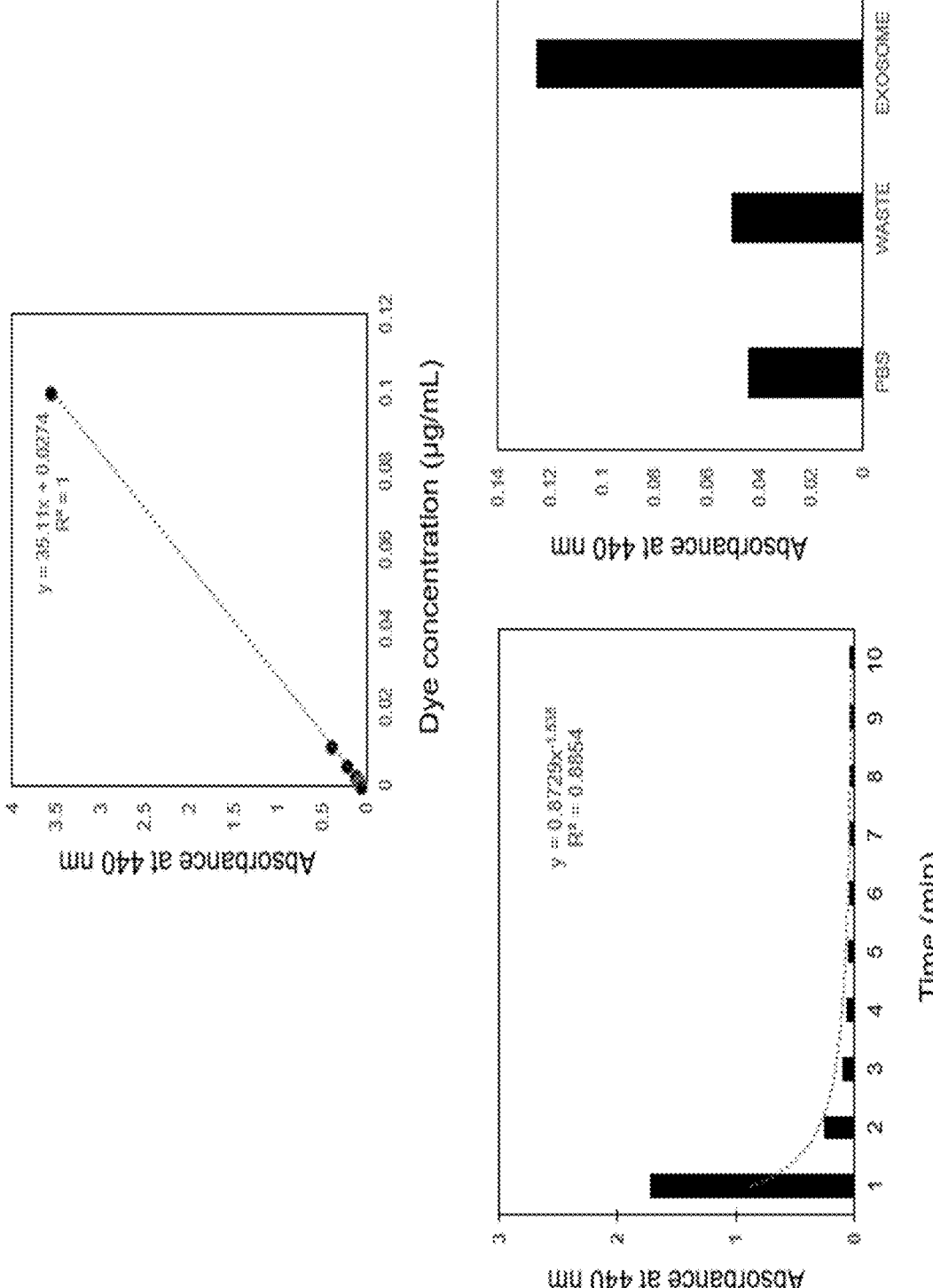
FIG. 5 shows the morphology and fluorescence expression test result of the DiD fluorescence labeled functional exosome.

After the above process, a washing process was performed to remove the remaining fluorescence labeling materials. As illustrated in FIG. 4, all clamps were removed. Pump 1 was operated at a speed of 10 to 250 cc/min for 1 minute to 10 minutes, and Pump 2 was operated at a speed of 5 to 10 to 50 cc/min for 1 minute to 10 minutes. Pump 1 was used for a use of the mixed solution to circulate the TFF and reservoir and Pump 2 was used for a use to deliver PBS for washing to the reservoir, and a use to collect the waste solution comprising the remaining fluorescence labeling materials, respectively. During the process, exosomes larger than membrane pores of the TFF filter were not filtered by the filter, but fluorescence labeling materials smaller than membrane pores were filtered, and therefore, unreacted fluorescence labeling materials which did not react with exosomes were removed and only the fluorescence labeled exosomes could be obtained. In order to confirm the cleaning effect, samples were taken by 1 mL per 1 minute, and the absorbance was measured at 450 nm using a UV-visible spectrophotometer. The finally separated exosomes and waste and PBS were collected by unit volume, and the absorbance at 450 nm was measured in the same manner (FIG. 5).

(2) Production of Fluorescence Labeled Functional Exosomes Using Ultra-High Centrifugation Method (Comparative Example 1)

The mixture of exosomes and fluorescence labeling materials was produced by the same method as the (1). Specifically, exosomes 1 mL at a concentration of $5.0 \times 10^9$ particle/mL and fluorescence labeling materials of 100 uL (Vybrant™ DiD Cell-Labeling Solution, ThermoFisher Scientific, V22887) were transferred to a 1.5 mL tube. The mixture was diluted in DPBS in a volume of 10 times to 100 times, and was poured into a reservoir in the TFF device, respectively, and mixed.

Figure 6:
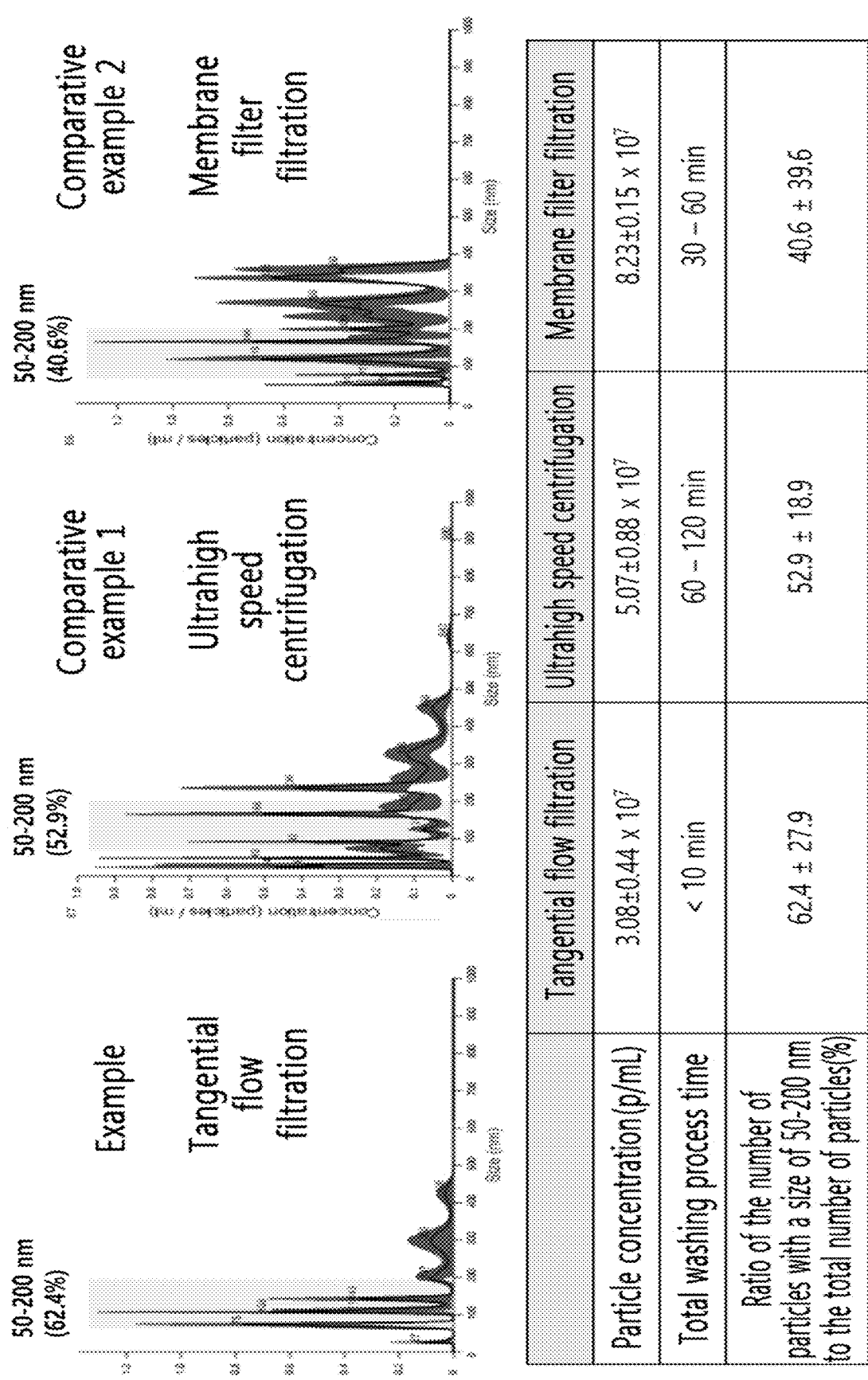
FIG. 6 is graphs which show the ratio of the number of particles having a size of 50-200 nm among the finally obtained particles by tangential flow filtration, ultra-high speed centrifugation and membrane filter filtration processes.
Figure 7:
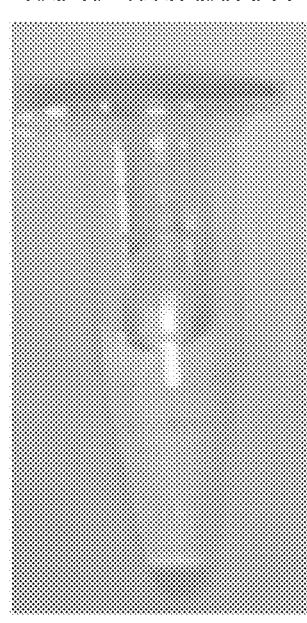
FIG. 7 shows the result of recovering fluorescence labeled exosomes produced by the tangential flow filtration, ultra-high speed centrifugation and membrane filter filtration processes with a 1.5 mL tube.
Figure 7:
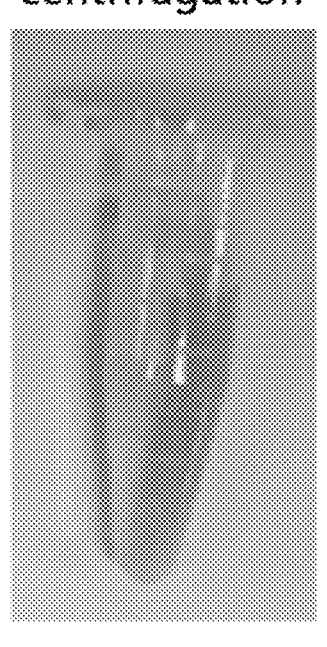
Figure 7:
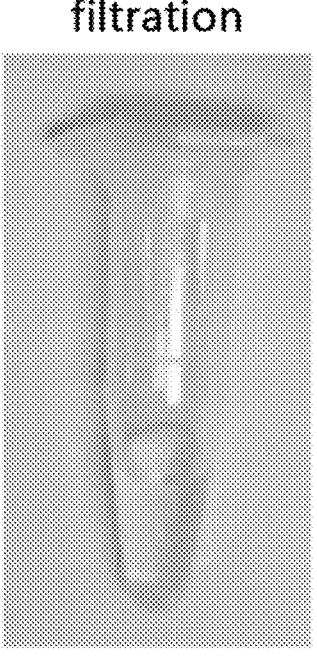

Then, the mixture was centrifuged at a rate of 80,000×g to 150,000×g, and the fluorescence labeled exosomes were spun-down. The fluorescence labeled exosomes were dispersed in DPBS of 1 mL to obtain a fluorescence labeled exosome solution (FIGS. 6, 7).

(3) Production of Fluorescence Labeled Functional Exosomes Using Membrane Filter Filtration Method (Comparative Example 2)

The mixture of exosomes and fluorescence labeling materials was produced by the same method as the (1). Specifically, exosomes 1 mL at a concentration of $5.0 \times 10^9$ particle/mL and fluorescence labeling materials of 100 uL (Vybrant™ DiD Cell-Labeling Solution, ThermoFisher Scientific, V22887) were transferred to a 1.5 mL tube. The mixture was diluted in DPBS in a volume of 10 times to 100 times, and was poured into a reservoir in the TFF device, respectively, and mixed.

Then, the mixture was centrifuged using a membrane filter having a 3 to 50 kDa filtering ability (Amicon® Ultra-15 Centrifugal Filter Units, Merck) at a rate of 1,000×g to 4,000×g for 30 minutes, and the fluorescence labeled exosomes were concentrated and purified. The fluorescence labeled exosomes were recovered with a 1.5 mL tube to obtain a fluorescence labeled exosome solution (FIGS. 6, 7).

5. Fluorescence Labeled Functional Exosome Properties Analysis

Figure 8:
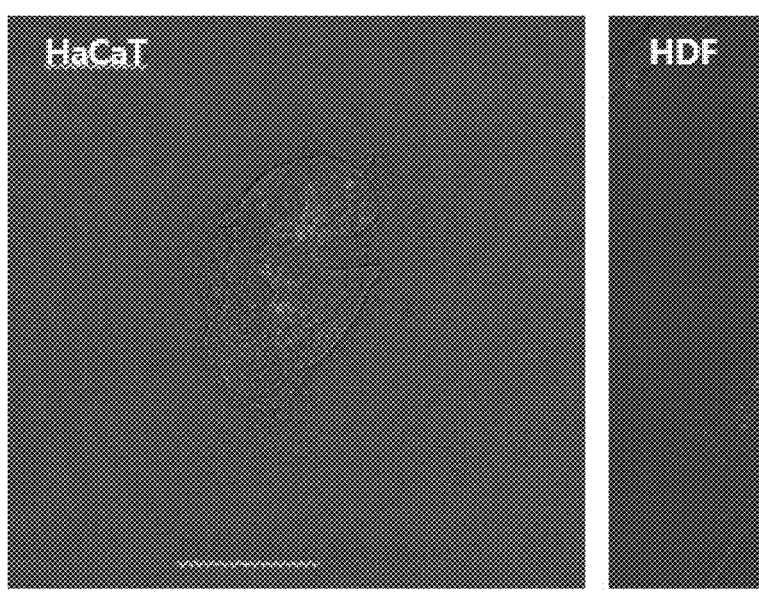
FIG. 8 shows the result of confirming intracellular penetration of the fluorescence labeled exosomes using a confocal fluorescence microscope.
Figure 8:
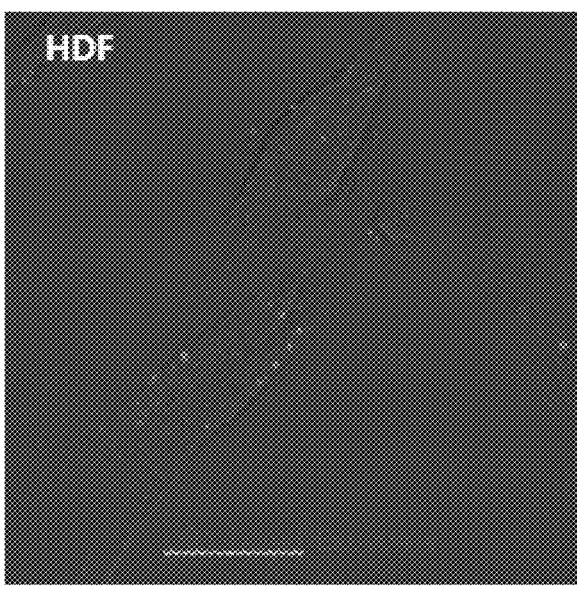

In order to confirm the fluorescence labeling ability of the fluorescence labeled functional exosomes produced in the 4(1), DPBS 1 mL in which $10^8$ to $10^{10}$ exosomes were dispersed and a cell culture solution 9 mL were mixed, and treated to human keratinocytes (HaCaT) for 1 hour. For the human keratinocytes treated by exosomes, intracellular penetration of the fluorescence labeled exosomes was confirmed using a confocal fluorescence microscope (FIG. 8).

6. Production of PEGylated Functional Exosomes Using Tangential Flow Filtration Method By the similar method to the 4(a), PEGylated exosomes were produced. Exosomes 1 mL at a concentration of $5.0 \times 10^9$ particle/mL and 1 to 1,000 mg/mL polyethylene glycol (PEG) of 10 uL were transferred to a 1.5 mL tube. The mixture was diluted in DPBS in a volume of 10 times to 100 times, and was poured into a reservoir in the TFF device, respectively, and mixed. In order to induce chemical binding of exosomes and PEG, a 1-Ethyl-3-(3-dimethylaminopropyl)carbodiimide (EDC)/N-hydroxysuccinimide (NHS) cross-linking process was performed. EDC 500 μL of 1 to 100 mM and NHS 500 μL at the same concentration were added to the exosomes/PEG mixture, and reacted in the reservoir for about 1 to 30 minutes.

After the above process, a washing process was performed to remove the remaining fluorescence labeling materials. As illustrated in FIG. 4, all clamps were removed. Pump 1 was operated at a speed of 10 to 250 cc/min for 30 minutes to 3 hours, and Pumps 2 and 3 were operated at a speed of 5 to 10 to 50 cc/min for 30 minutes to 3 hours. Pump 1 was used for a use of the mixed solution to circulate the TFF and reservoir, and Pump 2 and Pump 3 were used for a use to deliver PBS for washing to the reservoir, and a use to collect the waste solution comprising the remaining fluorescence labeling materials, respectively. During the process, exosomes larger than membrane pores of the TFF filter were not filtered by the filter, but chemical substances and the like smaller than membrane pores were filtered, and therefore, unreacted materials which did not react with exosomes were removed and only the fluorescence labeled exosomes could be obtained.

7. PEGylated Functional Exosome Properties Analysis

Figure 9:
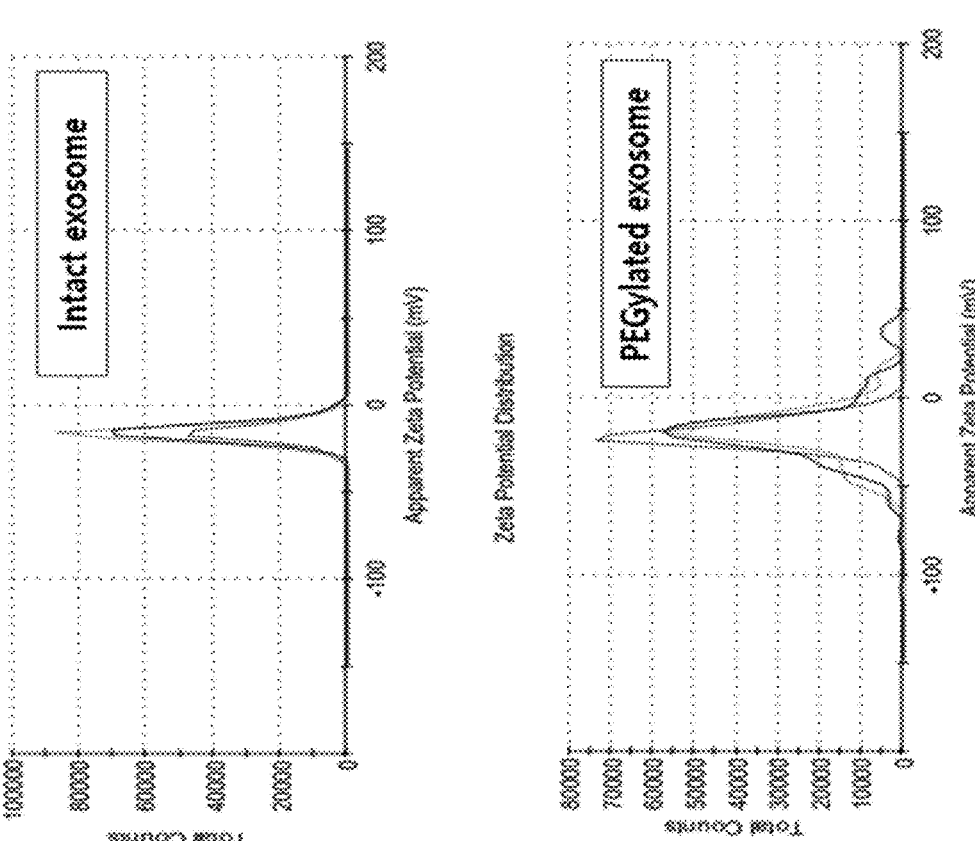
FIG. 9 shows the result of confirming the change in physical properties of the PEGylated exosomes produced by the tangential flow filtration process by zeta-potential.
Figure 10:
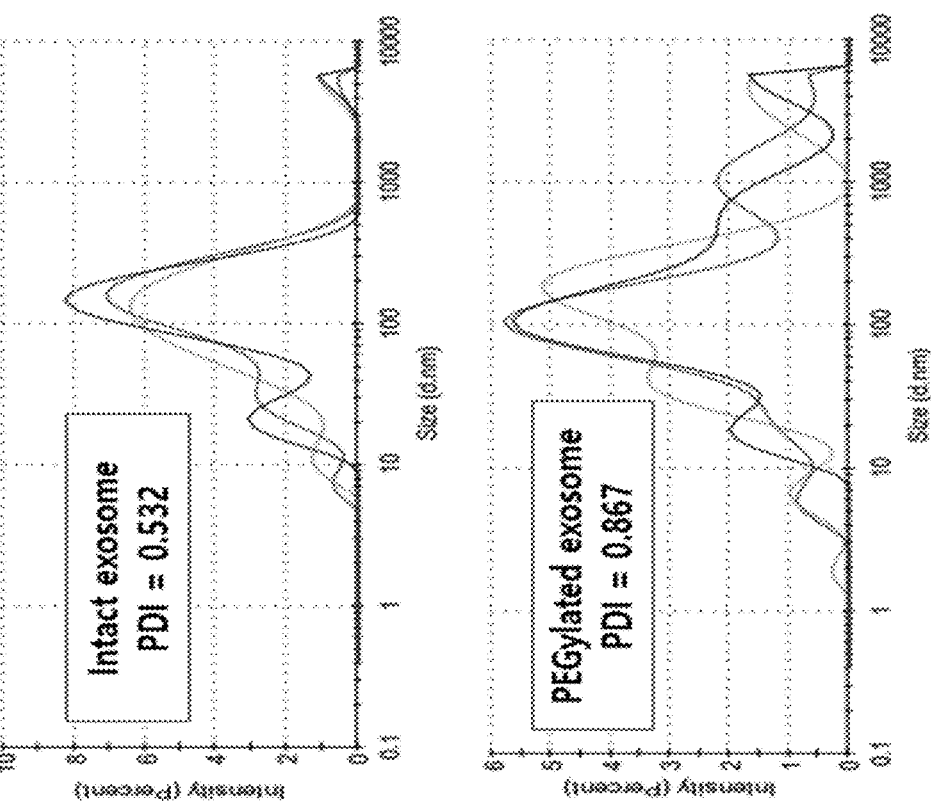
FIG. 10 shows the result of confirming the change in physical properties of the PEGylated exosomes produced by the tangential flow filtration by DLS.

The change in physical properties of the exosomes extracted from the human adipose derived stem cells through the 6 was confirmed by DLS and zeta-potential, thereby confirming whether the surface of the exosome particles was modified. It could be confirmed that the PEGylated functional exosomes had a larger particle size distribution compared to untreated exosomes (FIGS. 9, 10).

8. Production of Drug Loading Functional Exosomes Using Tangential Flow Filtration Method Drug loading exosomes were produced and purified by the similar method to the 4(a). To exosomes 1 mL at a concentration of $5.0 \times 10^9$ particle/mL, doxorubicin 100 μL of 1 to 1,000 μg was added. The mixture was diluted in DPBS in a volume of 10 times to 100 times, and was poured in a single-use bag in the TFF device, respectively, and mixed. For loading of drugs in exosomes, the process was progressed while the single-used bag in which the mixture was loaded was immersed in a sonication water bath maintained at 4° C. or lower.

A process of reacting by circulating the mixture of exosomes and drugs was carried out using the TFF device illustrated in FIG. 3. Then, the single-use bag was kept in a water batch where mild sonication was occurring. The tube connected to the P (Permeate) direction of the TFF filter and PBS for washing blocked the tube connected to the reservoir with a clamp to prevent reactants from escaping to the outside or external buffer from being mixed. Pump 1 was operated at a speed of 10 to 100 cc/min for 10 seconds to 1 hour, so that the mixed solution of the exosomes and fluorescence labeling materials in the reservoir circulated inside the TFF filter. In the process, the drugs were loaded in the exosomes.

After the above process, a washing process was performed to remove the remaining drugs. As illustrated in FIG. 4, all clamps were removed. Pump 1 was operated at a speed of 10 to 250 cc/min for 30 minutes to 3 hours, and Pumps 2 and 3 were operated at a speed of 5 to 10 to 50 cc/min for 30 minutes to 3 hours. Pump 1 was used for a use of the mixed solution to circulate the TFF and reservoir, and Pump 2 and Pump 3 were used for a use to deliver PBS for washing to the reservoir, and a use to collect the waste solution comprising the remaining fluorescence labeling materials, respectively. During the process, exosomes larger than membrane pores of the TFF filter were not filtered by the filter, but drugs smaller than membrane pores were filtered, and therefore, drugs not loaded on exosomes were removed and only the fluorescence labeled exosomes could be obtained.

9. Drug Loaded Functional Exosome Properties Analysis

Figure 11:
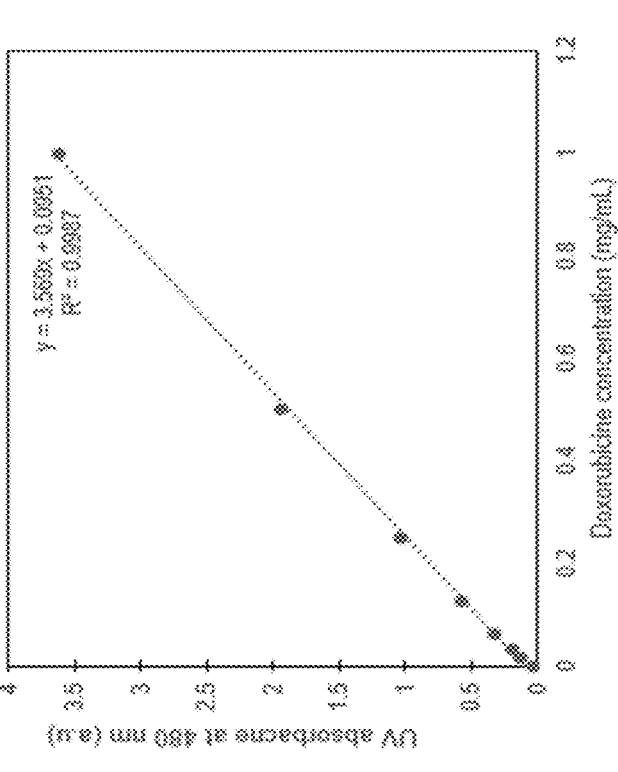
FIG. 11 shows the result of confirming drug loading inside the exosomes of DPBS 1 mL in which $10^8$ to $10^{10}$ exosomes are dispersed using a UV-visible spectrophotometer.

In order to confirm the drug loading amount of the drug-loaded exosomes, DPBS 1 mL in which $10^8$ to $10^{10}$ exosomes were dispersed was used to confirm drug loading inside the exosomes using a UV-visible spectrophotometer (FIG. 11). According to FIG. 11, it was confirmed that doxorubicin of about 20 μg was loaded in exosome $5 \times 10^9$ particles.

Figure 12:
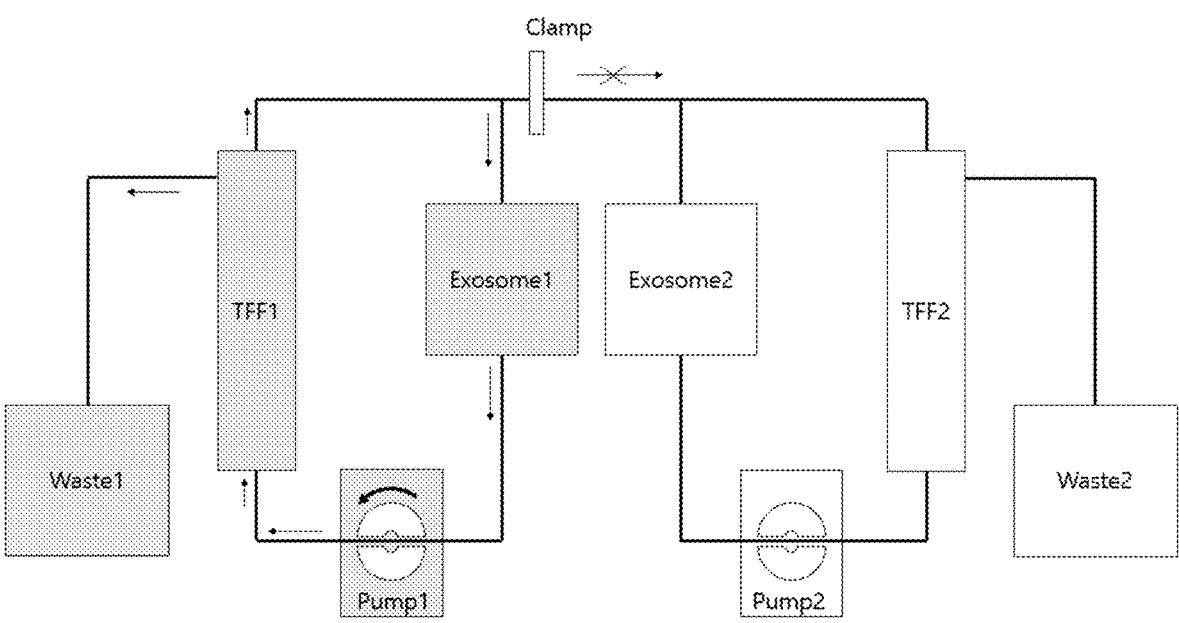
FIG. 12 is a schematic diagram which shows a process for producing functional exosomes from a cell culture solution using a continuous TFF process.
Figure 13:
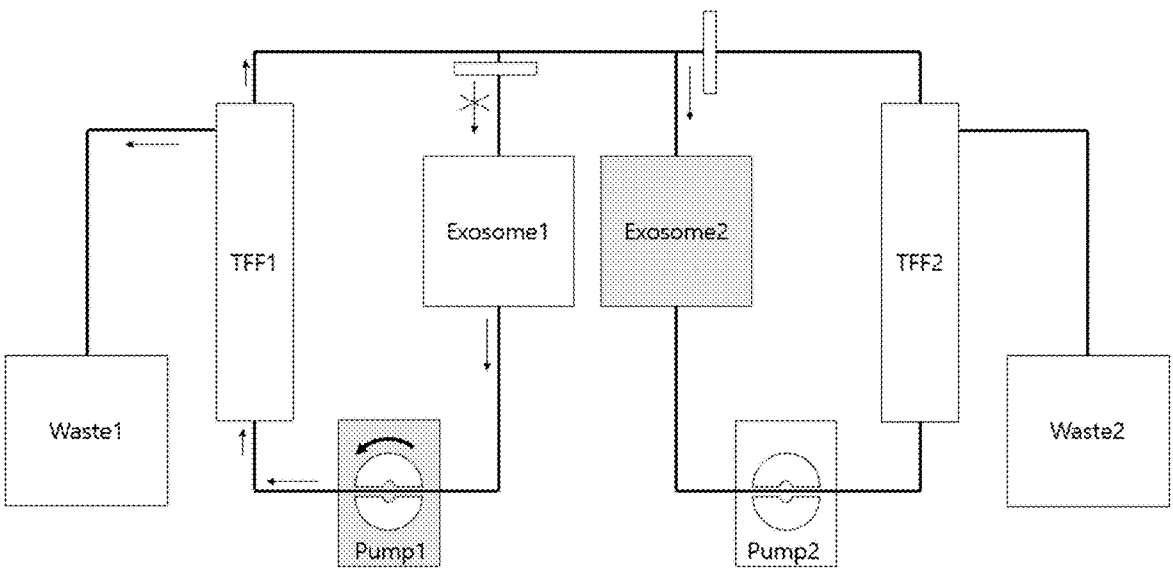
FIG. 13 is a schematic diagram which shows a process for producing functional exosomes from a cell culture solution using a continuous TFF process.
Figure 14:
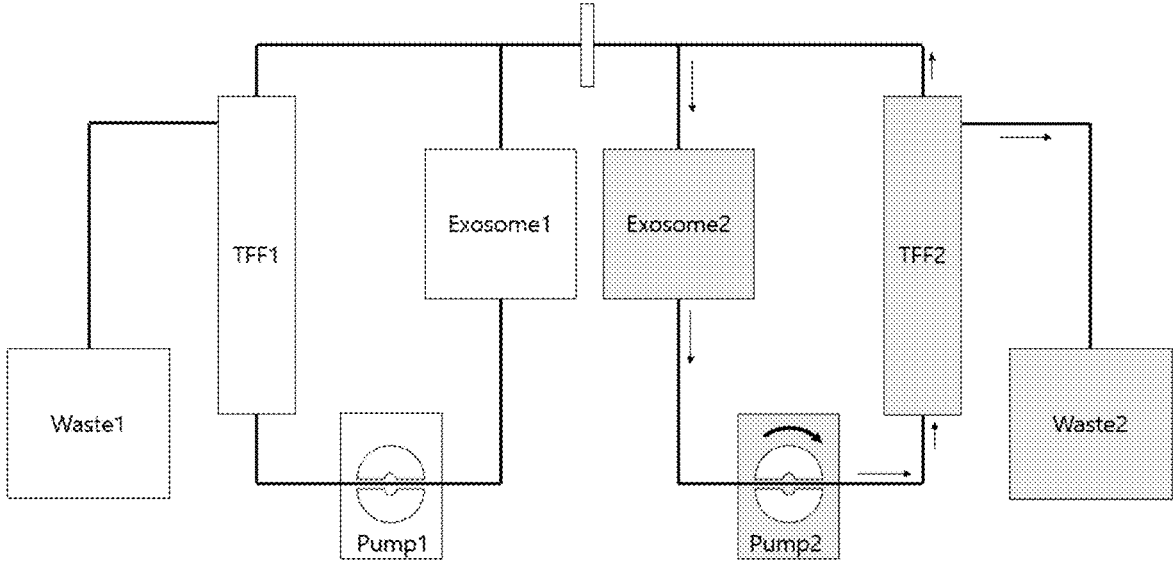
FIG. 14 is a schematic diagram which shows a process for producing a high concentration of functional exosomes using a continuous TFF process.
Figure 15:
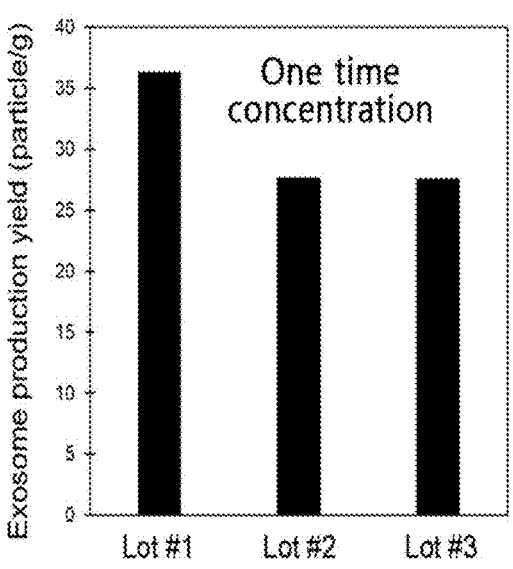
FIG. 15 shows the result of confirming the yield of exosomes obtained through the continuous TFF process as the amount of exosomes and proteins produced compared to the initial CM amount.
Figure 15:
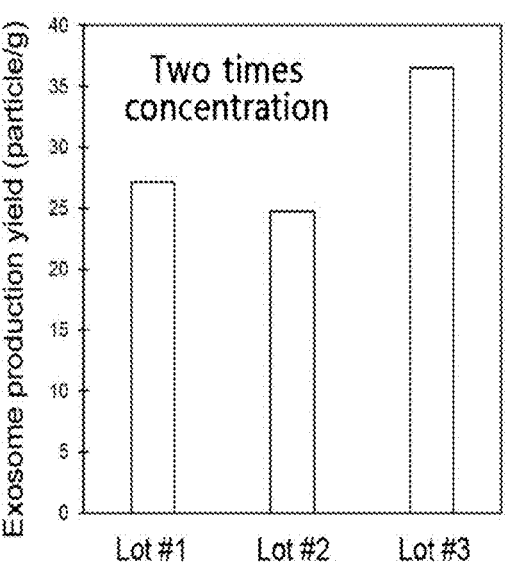

10. Extraction of Human Adipose Derived Stem Cell Exosomes at a High Concentration Using a Continuous TFF Process From the human adipose derived stem cell culture solution obtained in the 1, exosomes were extracted and purified using a continuous tangential flow filtration system. As a filter of the primary tangential flow filtration method, a filter having a 100 or 500 kDa filtering ability was used, and the cell culture solution was concentrated by 10 times or 100 times to recover exosomes. To increase the exosome purity, the recovered exosomes were diluted in DPBS in a volume of 10 times to 100 times, and concentrated using a filter having a 100 or 500 kDa filtering ability. The extraction process was illustrated in FIGS. 12, 13 and 14. The yield of the exosomes obtained through the continuous TFF process was confirmed by the amount of produced exosomes and proteins compared to the initial CM amount (FIG. 15).

The invention claimed is:

1. A method of preparing functional exosomes by modifying exosomes with functional materials using a tangential flow filtration (TFF) device, wherein the method comprises the following steps:

a reaction step of circulating and mixing exosomes and functional materials inside the TFF device;

a filtration and concentration step including removing unreacted functional materials; and a washing step of substituting a solvent of the mixed solution;

wherein the reaction step is performed by allowing the exosomes and functional materials to circulate between a reservoir and a TFF filter inside the TFF device by blocking a tube connected to a permeate (P) direction of the TFF filter and a tube connected to the reservoir, wherein the filtration and concentration step and the washing step are performed simultaneously by opening both the tube connected to the P direction of the TFF filter and the tube connected to the reservoir, wherein the reaction step, the filtration and concentration step, and the washing step are performed using a first TFF device.

2. The method according to claim 1, wherein the functional materials are biocompatible polymers, protein drugs, chemical drugs, and/or labeled molecules.

3. The method according to claim 1, wherein the reaction step of circulating and mixing exosomes and functional materials is performed by a pump of the TFF device.

4. The method according to claim 1, wherein the method comprises the reaction step, the filtration and concentration step and the washing step continuously using the TFF device.

5. The method according to claim 1, wherein the method is for large-scale production of the functional exosomes.

6. The method according to claim 1, wherein the method further comprises a step of injecting concentrated functional exosomes obtained from the first TFF device into a multiple TFF continuous concentration device to further concentrate the exosomes, wherein the multiple TFF continuous concentration device comprises n TFF devices, and the n TFF devices are connected to form one closed system isolated from the outside, and n concentration processes are continuously performed in the one closed system, and wherein n is an integer of 1 to 10.

* * * * *